US 12,105,110 B2

(12) United States Patent
Hollingsworth

(10) Patent No.: US 12,105,110 B2
(45) Date of Patent: Oct. 1, 2024

(54) TRUE VAPOR PRESSURE AND FLASHING DETECTION APPARATUS AND RELATED METHOD

(71) Applicant: MICRO MOTION, INC., Boulder, CO (US)

(72) Inventor: Justin Craig Hollingsworth, Fort Collins, CO (US)

(73) Assignee: MICRO MOTION, INC., Boulder, CO (US)

( * ) Notice: Subject to any disclaimer, the term of this patent is extended or adjusted under 35 U.S.C. 154(b) by 86 days.

(21) Appl. No.: 17/630,707

(22) PCT Filed: Aug. 19, 2019

(86) PCT No.: PCT/US2019/047071
§ 371 (c)(1),
(2) Date: Jan. 27, 2022

(87) PCT Pub. No.: WO2021/034312
PCT Pub. Date: Feb. 25, 2021

(65) Prior Publication Data
US 2022/0260469 A1    Aug. 18, 2022

(51) Int. Cl.
*G01N 9/32* (2006.01)
*G01F 1/84* (2006.01)
*G01N 25/50* (2006.01)

(52) U.S. Cl.
CPC ............ *G01N 9/32* (2013.01); *G01F 1/8422* (2013.01); *G01F 1/8427* (2013.01); *G01F 1/8477* (2013.01); *G01N 25/50* (2013.01)

(58) Field of Classification Search
CPC ...................................................... G01N 9/32
See application file for complete search history.

(56) References Cited

U.S. PATENT DOCUMENTS

| | | | |
|---|---|---|---|
| 4,783,989 A | 11/1988 | Reed | |
| 5,637,791 A | 6/1997 | Alonso | |
| 5,963,292 A * | 10/1999 | Rivir | G01P 5/001 |
| | | | 73/147 |
| 9,525,103 B2 * | 12/2016 | Narita | H01L 33/20 |
| 9,995,612 B2 | 6/2018 | Murakami | |
| 2014/0034145 A1 | 2/2014 | Alan | |

FOREIGN PATENT DOCUMENTS

| | | |
|---|---|---|
| EP | 3153827 A1 | 4/2017 |
| WO | 2012170020 A1 | 12/2012 |
| WO | 2019094038 A1 | 5/2019 |

OTHER PUBLICATIONS

Osterman, Aljaz et al., Infrared Thermography of Cavitation Thermal Effects in Water, Journal of Mechanical Engineering, Sep. 2010, p. 527-534; https://www.researchgate.net/publication/235339007.

* cited by examiner

*Primary Examiner* — Erika J. Villaluna
(74) *Attorney, Agent, or Firm* — The Ollila Law Group LLC

(57) ABSTRACT

A method of determining vapor pressure of a fluid is provided. The method comprises the step of providing a meter having meter electronics, wherein the meter comprises at least one of a flowmeter and a densitometer. A process fluid is flowed through the meter. A low-pressure location associated with the meter is provided. The pressure of the process fluid is adjusted until flashing is detectable at the low-pressure location. The true vapor pressure of the process fluid is calculated at an instant where flashing is detected.

12 Claims, 5 Drawing Sheets

TRUE VAPOR PRESSURE AND FLASHING DETECTION APPARATUS AND RELATED METHOD

TECHNICAL FIELD

The present invention relates to vibratory meters, and more particularly, to a method and apparatus for real-time vapor pressure determination.

BACKGROUND OF THE INVENTION

Reid Vapor Pressure (RVP) is one of the most widely recognized properties for measuring and enforcing fuel quality standards. True vapor pressure is an important property in applications which handle flow and storage of volatile fluids such as gasoline, natural gas liquids, and liquid petroleum gas. Vapor pressure provides an indication of how volatile fluids may perform during handling, and further indicates conditions under which bubbles will likely form and pressure will likely build. As such, vapor pressure measurement of volatile fluids increases safety and prevents damage to transport vessels and infrastructure.

If the vapor pressure of a fluid is too high, cavitation during pumping and transfer operations may occur. Furthermore, vessel or process line vapor pressure may potentially rise beyond safe levels due to temperature changes. It is therefore often required that RVP be known prior to storage and transport.

Typically, RVP is determined by capturing samples and removing them to a laboratory for testing to determine the value from the sample. This poses difficult issues for regulatory fuel quality standards enforcement because of the delay in obtaining final results, the cost of maintaining a lab, and the safety and legal evidence vulnerabilities associated with sample handling. True vapor pressure is often determined by this same process, followed by a conversion from the RVP determined in a lab to the true vapor pressure at flowing temperature by relying on lookup tables and databases based on empirical measurements.

A need therefore exists for an in-line device or system that can measure true vapor pressure and/or RVP on a continuous, real-time, basis under process conditions. This is provided by the present embodiments, and an advance in the art is achieved. On-site measurement is more reliable, as it obviates the need for the periodic sampling and fully eliminates the risk of fluid property changes between the time of sample collection and laboratory assay. Furthermore, safety is improved by having real-time measurements, as unsafe conditions may be remedied immediately. Additionally, money is saved, as regulatory enforcement may be conducted via simple on-site checks, wherein inspection and enforcement decisions may be made with little delay or process cessation.

SUMMARY OF THE INVENTION

A method of determining vapor pressure of a fluid is provided according to an embodiment. The method comprises the step of providing a meter having meter electronics, wherein the meter comprises at least one of a flowmeter and a densitometer. A process fluid is flowed through the meter, and a low-pressure location associated with the meter is provided. A temperature of the process fluid at the low-pressure location is measured. The static pressure of the process fluid is adjusted until flashing is detectable at the low-pressure location. The true vapor pressure of the process fluid at an instance where flashing is detectable is determined.

A system for determining true vapor pressure of a process fluid is provided according to an embodiment. The system comprises a meter including at least one of a flowmeter and a densitometer. A low-pressure location is associated with the meter. A pressure regulator is in fluid communication with the meter. A pressure sensor is in fluid communication with the process fluid. A temperature sensor is configured to measure a temperature at the low-pressure location. Meter electronics is in communication with the meter and the pressure sensor, wherein the meter electronics is configured to control the pressure regulator to adjust the static pressure of the process fluid until flashing at the low-pressure location is detected and calculate a true vapor pressure of the process fluid at an instance where flashing is detectable.

Aspects

According to an aspect, a method of determining vapor pressure of a fluid is provided. The method comprises the step of providing a meter having meter electronics, wherein the meter comprises at least one of a flowmeter and a densitometer. A process fluid is flowed through the meter, and a low-pressure location associated with the meter is provided. A temperature of the process fluid at the low-pressure location is measured. The static pressure of the process fluid is adjusted until flashing is detectable at the low-pressure location. The true vapor pressure of the process fluid at an instance where flashing is detectable is determined.

Preferably, measuring the temperature comprises IR thermography.

Preferably, detecting the flashing comprises optical analysis.

Preferably, the low-pressure location comprises a flowmeter manifold.

Preferably, the low-pressure location comprises a differential pressure element.

Preferably, the method comprises the steps of measuring the temperature of the process fluid and calculating the Reid Vapor Pressure from the temperature and the true vapor pressure.

Preferably, the method comprises the steps of measuring a vapor:liquid ratio at a time point where the Reid vapor pressure is measured and associating the vapor:liquid ratio with the Reid vapor pressure at the time point the Reid vapor pressure is measured.

According to an aspect, a system for determining true vapor pressure of a process fluid is provided. The system comprises a meter comprising at least one of a flowmeter and a densitometer. A low-pressure location is associated with the meter. A pressure regulator is in fluid communication with the meter. A pressure sensor is in fluid communication with the process fluid. A temperature sensor is configured to measure a temperature at the low-pressure location. Meter electronics is in communication with the meter and the pressure sensor, wherein the meter electronics is configured to control the pressure regulator to adjust the static pressure of the process fluid until flashing at the low-pressure location is detected and calculate a true vapor pressure of the process fluid at an instance where flashing is detectable.

Preferably, the temperature sensor comprises an IR thermograph.

Preferably, an optical sensor is configured to detect flashing.

Preferably, the low-pressure location comprises a flowmeter manifold.

Preferably, the low-pressure location comprises a differential pressure element.

Preferably, the meter electronics is configured to measure a vapor:liquid ratio at a time point where the Reid vapor pressure is measured and associating the vapor:liquid ratio with the Reid vapor pressure at the time point where the Reid vapor pressure is measured.

Preferably, the meter comprises one or more conduits, at least one driver attached to the one or more conduits configured to generate a vibratory signal to the one or more conduits, and at least one pickoff attached to the one or more conduits configured to receive a vibratory signal from the one or more conduits.

DETAILED DESCRIPTION OF THE INVENTION

Figure 1:
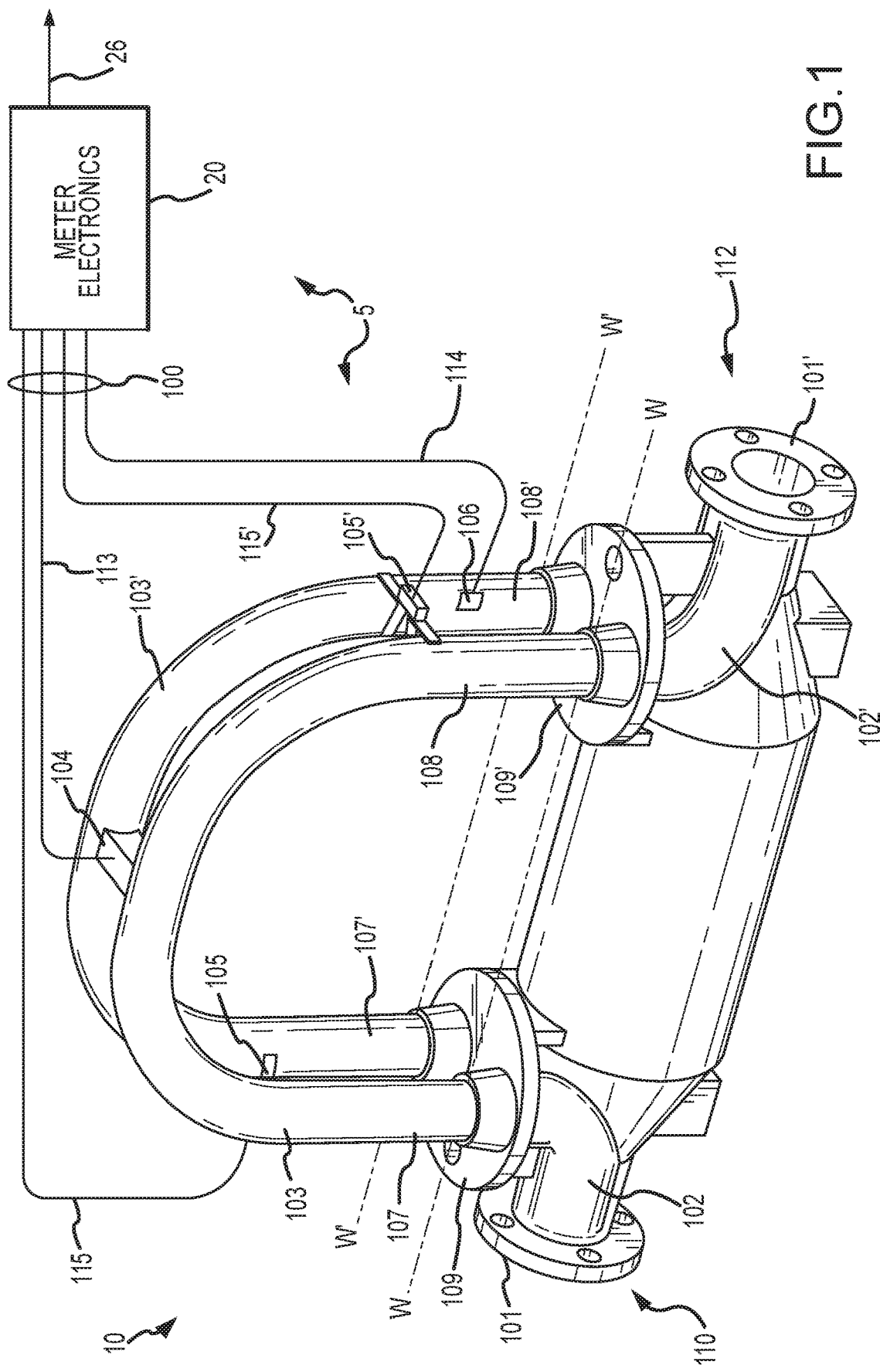
FIG. 1 illustrates a flowmeter sensor assembly according to an embodiment.

FIGS. 1-5 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Vibrating sensors, such as for example, vibrating densitometers and Coriolis flowmeters are generally known, and are used to measure mass flow and other information related to materials flowing through a conduit in the flowmeter or a conduit containing the densitometer. Exemplary flowmeters are disclosed in U.S. Pat. Nos. 4,109,524, 4,491,025, and Re. 31,450, all to J. E. Smith et al. These flowmeters have one or more conduits of a straight or curved configuration. Each conduit configuration in a Coriolis mass flowmeter, for example, has a set of natural vibration modes, which may be of simple bending, torsional, or coupled type. Each conduit can be driven to oscillate at a preferred mode.

Some types of mass flowmeters, especially Coriolis flowmeters, are capable of being operated in a manner that performs a direct measurement of density to provide volumetric information through the quotient of mass over density. See, e.g., U.S. Pat. No. 4,872,351 to Ruesch for a net oil computer that uses a Coriolis flowmeter to measure the density of an unknown multiphase fluid. U.S. Pat. No. 5,687,100 to Buttler et al., teaches a Coriolis effect densitometer that corrects the density readings for mass flow rate effects in a mass flowmeter operating as a vibrating tube densitometer.

Material flows into the flowmeter from a connected pipeline on the inlet side of the flowmeter, is directed through the conduit(s), and exits the flowmeter through the outlet side of the flowmeter. The natural vibration modes of the vibrating system are defined in part by the combined mass of the conduits and the material flowing within the conduits.

When there is no flow through the flowmeter, a driving force applied to the conduit(s) causes all points along the conduit(s) to oscillate with identical phase or with a small "zero offset", which is a time delay measured at zero flow. As material begins to flow through the flowmeter, Coriolis forces cause each point along the conduit(s) to have a different phase. For example, the phase at the inlet end of the flowmeter lags the phase at the centralized driver position, while the phase at the outlet leads the phase at the centralized driver position. Pickoffs on the conduit(s) produce sinusoidal signals representative of the motion of the conduit(s). Signals output from the pickoffs are processed to determine the time delay between the pickoffs. The time delay between the two or more pickoffs is proportional to the mass flow rate of material flowing through the conduit(s).

Meter electronics connected to the driver generate a drive signal to operate the driver and also to determine a mass flow rate and/or other properties of a process material from signals received from the pickoffs. The driver may comprise one of many well-known arrangements; however, a magnet and an opposing drive coil have received great success in the flowmeter industry. An alternating current is passed to the drive coil for vibrating the conduit(s) at a desired conduit amplitude and frequency. It is also known in the art to provide the pickoffs as a magnet and coil arrangement very similar to the driver arrangement. However, while the driver receives a current which induces a motion, the pickoffs can use the motion provided by the driver to induce a voltage. The magnitude of the time delay measured by the pickoffs is very small; often measured in nanoseconds. Therefore, it is necessary to have the transducer output be very accurate.

FIG. 1 illustrates a flowmeter 5, which can be any vibrating meter, such as a Coriolis flowmeter or densitometer, for example without limitation. The flowmeter 5 comprises a sensor assembly 10 and meter electronics 20. The sensor assembly 10 responds to mass flow rate and density of a process material. Meter electronics 20 are connected to the sensor assembly 10 via leads 100 to provide density, mass flow rate, and temperature information over path 26, as well as other information. The sensor assembly 10 includes flanges 101 and 101', a pair of manifolds 102 and 102', a pair of parallel conduits 103 (first conduit) and 103' (second conduit), a driver 104, a temperature sensor 106 such as a resistive temperature detector (RTD), and a pair of pickoffs 105 and 105', such as magnet/coil pickoffs, strain gages, optical sensors, or any other pickoff known in the art. The conduits 103 and 103' have inlet legs 107 and 107' and outlet legs 108 and 108', respectively. Conduits 103 and 103' bend in at least one symmetrical location along their length and are essentially parallel throughout their length. Each conduit 103, 103', oscillates about axes W and W', respectively.

The legs 107, 107', 108, 108' of conduits 103, 103' are fixedly attached to conduit mounting blocks 109 and 109' and these blocks, in turn, are fixedly attached to manifolds 102 and 102'. This provides a continuous closed material path through the sensor assembly 10.

When flanges 101 and 101' are connected to a process line (not shown) that carries the process material that is being measured, material enters a first end 110 of the flowmeter 5 through a first orifice (not visible in the view of FIG. 1) in flange 101, and is conducted through the manifold 102 to conduit mounting block 109. Within the manifold 102, the material is divided and routed through conduits 103 and 103'. Upon exiting conduits 103 and 103', the process material is recombined in a single stream within manifold 102' and is thereafter routed to exit a second end 112 connected by flange 101' to the process line (not shown).

Conduits 103 and 103' are selected and appropriately mounted to the conduit mounting blocks 109 and 109' so as to have substantially the same mass distribution, moments of inertia, and Young's modulus about bending axes W—W and W'—W', respectively. Inasmuch as the Young's modulus of the conduits 103, 103' changes with temperature, and this change affects the calculation of flow and density, a temperature sensor 106 is mounted to at least one conduit 103, 103' to continuously measure the temperature of the conduit. The temperature of the conduit, and hence the voltage appearing across the temperature sensor 106 for a given current passing therethrough, is governed primarily by the temperature of the material passing through the conduit. The temperature-dependent voltage appearing across the temperature sensor 106 is used in a well-known method by meter electronics 20 to compensate for the change in elastic modulus of conduits 103, 103' due to any changes in conduit 103, 103' temperature. The temperature sensor 106 is connected to meter electronics 20.

Both conduits 103, 103' are driven by driver 104 in opposite directions about their respective bending axes W and W' at what is termed the first out-of-phase bending mode of the flowmeter. This driver 104 may comprise any one of many well-known arrangements, such as a magnet mounted to conduit 103' and an opposing coil mounted to conduit 103, through which an alternating current is passed for vibrating both conduits. A suitable drive signal is applied by meter electronics 20, via lead 113, to the driver 104. It should be appreciated that while the discussion is directed towards two conduits 103, 103', in other embodiments, only a single conduit may be provided, or more than two conduits may be provided. It is also within the scope of the present invention to produce multiple drive signals for multiple drivers and for the driver(s) to drive the conduits in modes other than the first out-of-phase bending mode.

Meter electronics 20 receive the temperature signal on lead 114, and the left and right velocity signals appearing on leads 115 and 115', respectively. Meter electronics 20 produce the drive signal appearing on lead 113 to driver 104 and vibrate conduits 103, 103'. Meter electronics 20 process the left and right velocity signals and the temperature signal to compute the mass flow rate and the density of the material passing through the sensor assembly 10. This information, along with other information, is applied by meter electronics 20 over path 26 to utilization means. An explanation of the circuitry of the meter electronics 20 is not needed to understand the present invention and is omitted for brevity of this description. It should be appreciated that the description of FIG. 1 is provided merely as an example of the operation of one possible vibrating meter and is not intended to limit the teaching of the present invention.

A Coriolis flowmeter structure is described although it will be apparent to those skilled in the art that the present invention could be practiced on a vibrating tube or fork densitometer without the additional measurement capability provided by a Coriolis mass flowmeter.

Figure 2:
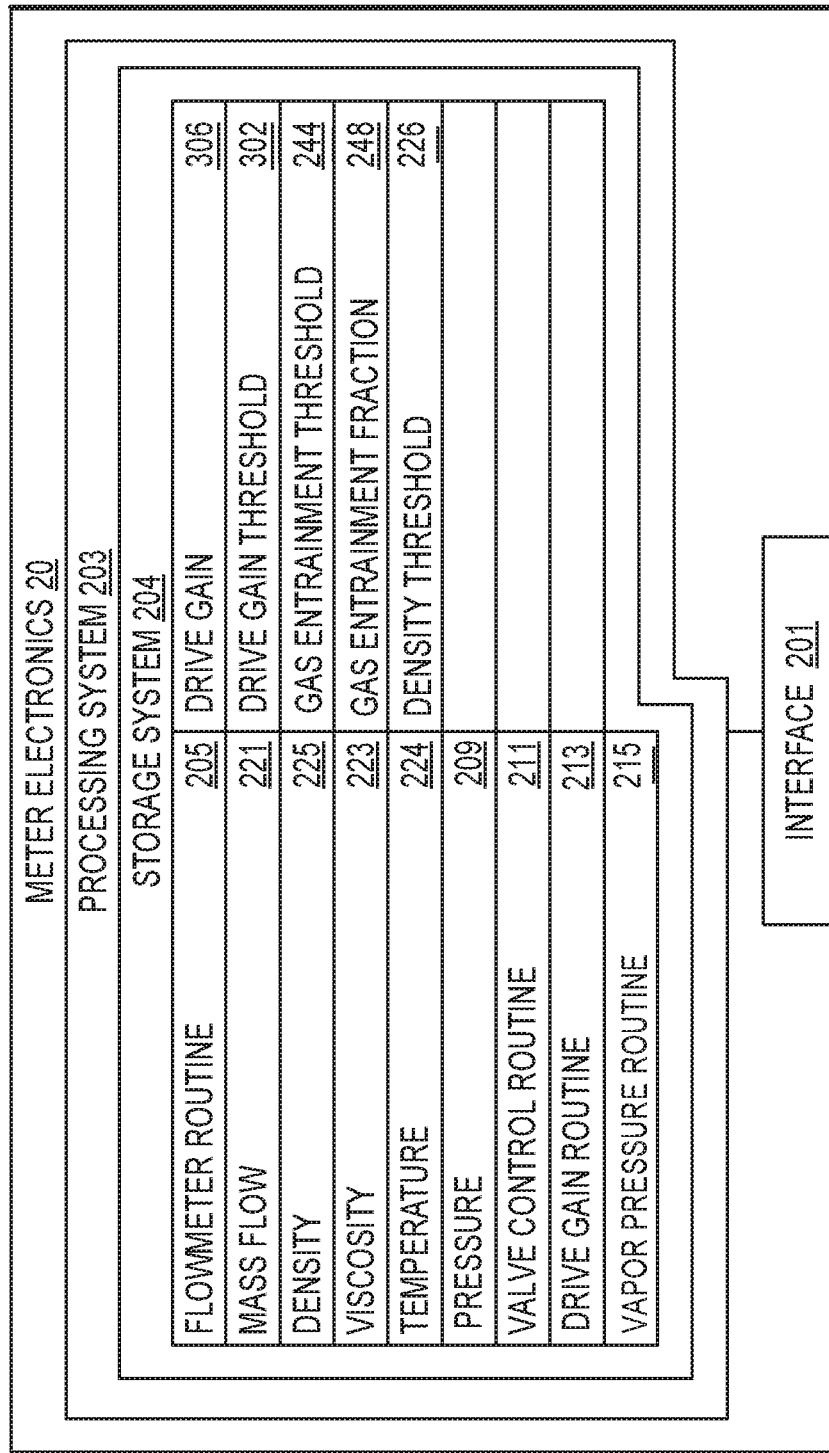
FIG. 2 illustrates meter electronics according to an embodiment.

FIG. 2 is a block diagram of the meter electronics 20 of flowmeter 5 according to an embodiment. In operation, the flowmeter 5 provides various measurement values that may be outputted including one or more of a measured or averaged value of mass flow rate, volume flow rate, individual flow component mass and volume flow rates, and total flow rate, including, for example, both volume and mass flow of individual flow components.

The flowmeter 5 generates a vibrational response. The vibrational response is received and processed by the meter electronics 20 to generate one or more fluid measurement values. The values can be monitored, recorded, saved, totaled, and/or output.

The meter electronics 20 includes an interface 201, a processing system 203 in communication with the interface 201, and a storage system 204 in communication with the processing system 203. Although these components are shown as distinct blocks, it should be understood that the meter electronics 20 can be comprised of various combinations of integrated and/or discrete components.

The interface 201 is configured to communicate with the sensor assembly 10 of the flowmeter 5. The interface 201 may be configured to couple to the leads 100 (see FIG. 1) and exchange signals with the driver 104, pickoff sensors 105 and 105', and temperature sensors 106, for example. The interface 201 may be further configured to communicate over the communication path 26, such as to external devices.

The processing system 203 can comprise any manner of processing system. The processing system 203 is configured to retrieve and execute stored routines in order to operate the flowmeter 5. The storage system 204 can store routines including a flowmeter routine 205, a valve control routine 211, a drive gain routine 213, and a vapor pressure routine 215. The storage system 204 can store measurements, received values, working values, and other information. In some embodiments, the storage system stores a mass flow (m) 221, a density (ρ) 225, a density threshold (226), a viscosity (μ) 223, a temperature (T) 224, a pressure 209, a drive gain 306, a drive gain threshold 302, a gas entrainment threshold 244, a gas entrainment fraction 248, and any other variables known in the art. The routines 205, 211, 213, 215 may comprise any signal noted, and other variables known in the art. Other measurement/processing routines are contemplated and are within the scope of the description and claims.

The flowmeter routine 205 can produce and store fluid quantifications and flow measurements. These values can comprise substantially instantaneous measurement values or can comprise totalized or accumulated values. For example, the flowmeter routine 205 can generate mass flow measurements and store them in the mass flow 221 storage of the storage system 204, for example. The flowmeter routine 205 can generate density 225 measurements and store them in the storage system 204, for example. The mass flow 221 and density 225 values are determined from the vibrational response, as previously discussed and as known in the art. The mass flow and other measurements can comprise a substantially instantaneous value, can comprise a sample, can comprise an averaged value over a time interval, or can comprise an accumulated value over a time interval. The time interval may be chosen to correspond to a block of time during which certain fluid conditions are detected, for example a liquid-only fluid state, or alternatively, a fluid state including liquids and entrained gas. In addition, other mass and volume flow and related quantifications are contemplated and are within the scope of the description and claims.

As noted, drive gain 306 may be utilized as the signal that indicates a no-flow/false totalizing condition. A drive gain threshold 302 may be used to distinguish between periods of flow, no flow, a monophasic/biphasic fluid phase boundary, and gas entrainment/mixed-phase flow. Similarly, a density threshold 226 applied to the density reading 225 may also be used, separately or together with the drive gain 306, to distinguish gas entrainment/mixed-phase flow. Drive gain 306 may be utilized as a metric for the sensitivity of the flowmeter's 5 conduit vibration to the presence of fluids of disparate densities, such as liquid and gas phases, for example, without limitation. The combined effect of damping on energy input and resulting amplitude is known as extended drive gain, which represents an estimate of how much power would be required to maintain target vibration amplitude, if more than 100% power were available:

$$\text{Extended Drive Gain} = \text{Drive Gain} * \frac{\text{Drive Target}}{\left(\frac{\text{Max(Left Pickoff, Right Pickoff)}}{\text{Frequency}}\right)} \quad (1)$$

It should be noted that, for purposes of the embodiments provided herein, that the term drive gain may, in some embodiments, refer to drive current, pickoff voltage, or any signal measured or derived that indicates the amount of power needed to drive the flow conduits 103, 103' at a particular amplitude. In related embodiments, the term drive gain may be expanded to encompass any metric utilized to detect multi-phase flow, such as noise levels, standard deviation of signals, damping-related measurements, and any other means known in the art to detect mixed-phase flow. In an embodiment, these metrics may be compared across the pick-off sensors 105 and 105' to detect a mixed-phase flow.

The vibrating conduits 103, 103' take very little energy to keep vibrating at their first resonant frequency, so long as all of the fluid in the tube is homogenous with regard to density. In the case of the fluid consisting of two (or more) immiscible components of different densities, the vibration of the tube will cause displacement of different magnitudes of each of the components. This difference in displacement is known as decoupling, and the magnitude of this decoupling has been shown to be dependent on the ratio of the densities of the components as well as the inverse Stokes number:

$$\text{Density Ratio} \equiv \frac{\rho_{fluid}}{\rho_{particle}} \quad (2)$$

$$\text{Inverse Stokes number} = \sqrt{\frac{2v_f}{\omega r^2}} \quad (3)$$

Where $\omega$ is the frequency of vibration, $v$ is the kinematic viscosity of the fluid, and $r$ is the radius of the particle. It should be noted that the particle may have a lower density than the fluid, as in the case of a bubble.

Decoupling that occurs between the components causes damping to occur in the vibration of the tube, requiring more energy to maintain vibration, or reducing the amplitude of vibration, for a fixed amount energy input.

Figure 3:
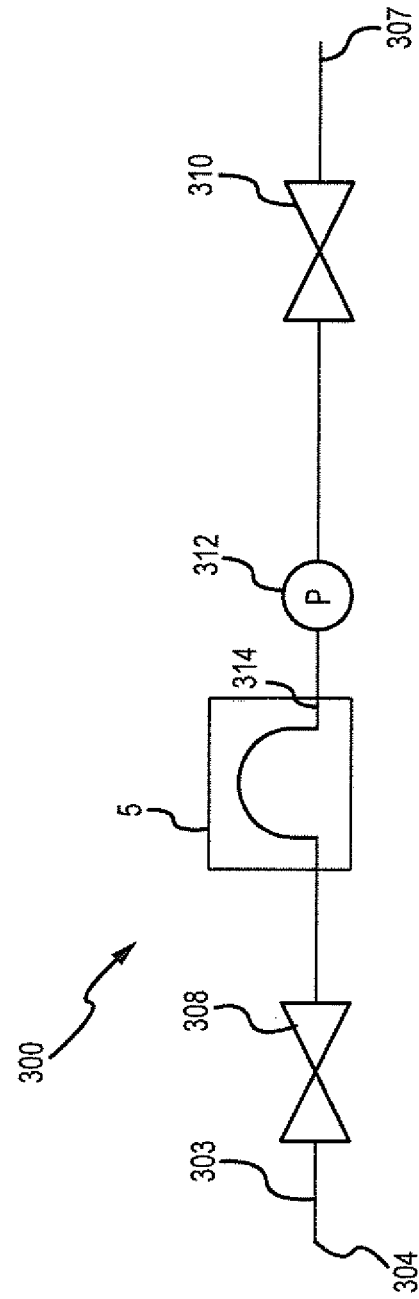
FIG. 3 illustrates a vapor pressure determination system according to an embodiment.
Figure 4:
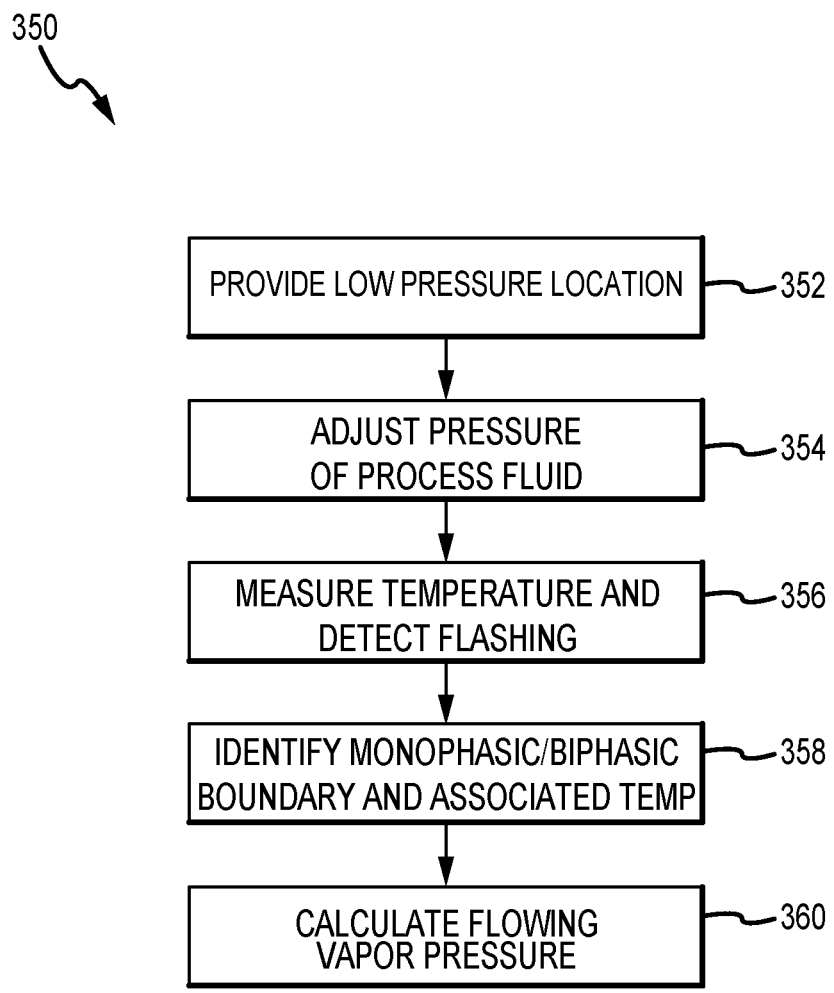
FIG. 4 illustrates a method of vapor pressure determination according to an embodiment.

Turning to FIG. 3, a vapor pressure determination system 300 is provided according to an embodiment. A process line 303 having an inlet 304 and an outlet 307 is provided, wherein the process line 303 is configured to carry a process fluid that enters the process line 303 through the inlet 304. An upstream pressure regulator 308 is provided that controls the fluid flow through the process line 303. A downstream pressure regulator 310 is provided that controls the fluid flow through the process line 303. A flowmeter 5 having meter electronics 20 is disposed between the upstream pressure regulator 308 and the downstream pressure regulator 310 and is configured to receive process fluid that passes through the upstream pressure regulator 308. A pressure sensor 312 and a temperature sensor 314 are also present in the system 300. Though the pressure sensor 312 and temperature sensor 314 are illustrated downstream of the flowmeter 5, these sensors 312, 314 may be situated before the flowmeter 5, or incorporated within the flowmeter 5.

Since the low-pressure-point is dictated by frictional pressure losses and the drop in static pressure due to velocity, and Bernoulli's principle in general, a velocity control system may, in an embodiment, control pressure. In such an embodiment, a variable speed pump and pressure control valve may, together, adjust fluid velocity. In this embodiment, the control valve may be located downstream of the meter, and the pump is located upstream of the meter, so that increasing the flow rate does not also increase the static pressure in the meter. Thus, the static pressure in the meter may be controlled by both reducing the static pressure with an upstream valve and also a pump downstream. Increasing the velocity in the meter also decreases the static pressure. The pressure in the meter tubes may be predicted by knowing the pressure upstream and downstream and the flow velocity. The pressure in the meter is lowered by increasing pump speed or closing the valve until flashing is detected.

Meter electronics 20 is in communication with the upstream pressure regulator 308, downstream pressure regulator 310, pressure sensor 312, and temperature sensor 314. Meter electronics 20 may control the upstream pressure regulator 308 and downstream pressure regulator 310. Meter electronics 20 receives a pressure measurement from pressure sensor 312, and a temperature measurement from the temperature sensor 314. The meter electronics 20 is configured to monitor the pressure of the process fluid and reduce its pressure until the flowmeter 5 detects the introduction of a second phase, which indicates that the vapor pressure has been reached. In an embodiment, only a single pressure regulator 308 is present. Studies have shown the high precision temperature measurement is capable of detecting very early signs of flashing/cavitation. In embodiments, extremely localized decreases in temperature are detected, which indicate a phase change (due to latent heat of vaporization). Flashing is therefore detected at the location and time of first occurrence.

In embodiments, it is the geometry of the vibrating tube sensor or a dedicated pressure drop element that allows for accurate predictions of where the flashing will first occur. This allows a temperature measurement to be focused on that point. In embodiments, a low-pressure location is therefore provided 352, as illustrated in the method 350 of FIG. 4.

If the process fluid is single-phase under normal process conditions, the pressure can be reduced by partially closing the upstream pressure regulator 308, for example, as shown in step 354. In an embodiment, high resolution IR thermography is utilized to detect temperature changes at the low-pressure location. In an embodiment, IR thermography is combined with optical sensors and analysis to detect the occurrence of flashing. Although IR thermography is specifically noted, since the precise location of first flashing is known with accuracy, it is contemplated that other temperature measurement devices with sufficient sensitivity may be used.

The low-pressure location, and therefore the point at which flashing will occur first, is generally near the outlet manifold 102' on a vibrating tube sensor. Flashing occurs at that location substantially before it is detectable by conventional methods. Therefore, temperature measurements at this location allow for detection of the very beginnings of flashing 356. Flashing detection allows the monophasic/biphasic fluid phase boundary to be identified 358. A temperature associated with flashing is measured and recorded. In step 360, the true vapor pressure is calculated, taking into account the temperature at the point flashing was detected.

In an embodiment, a temperature measurement device that is sensitive enough to detect such a change is located in the flowmeter manifold.

In an embodiment, part of a vapor pressure measurement may comprise specifying at what vapor:liquid ratio the vapor pressure is measured. With this method, flashing at 0% vapor is detectable. Other measurements in the vibrating tube sensor may also be used to determine the vapor:liquid ratio as it increases, so that the vapor pressure could be measured at multiple vapor:liquid ratios, starting at 0%.

In an embodiment, if it is deemed unnecessary to measure the vapor pressure at vapor: liquid ratios other than 0%, a differential pressure element (315) may be provided so that the required pressure drop is present. Temperature measurement or thermography at this point is utilized for flashing detection.

Figure 5:
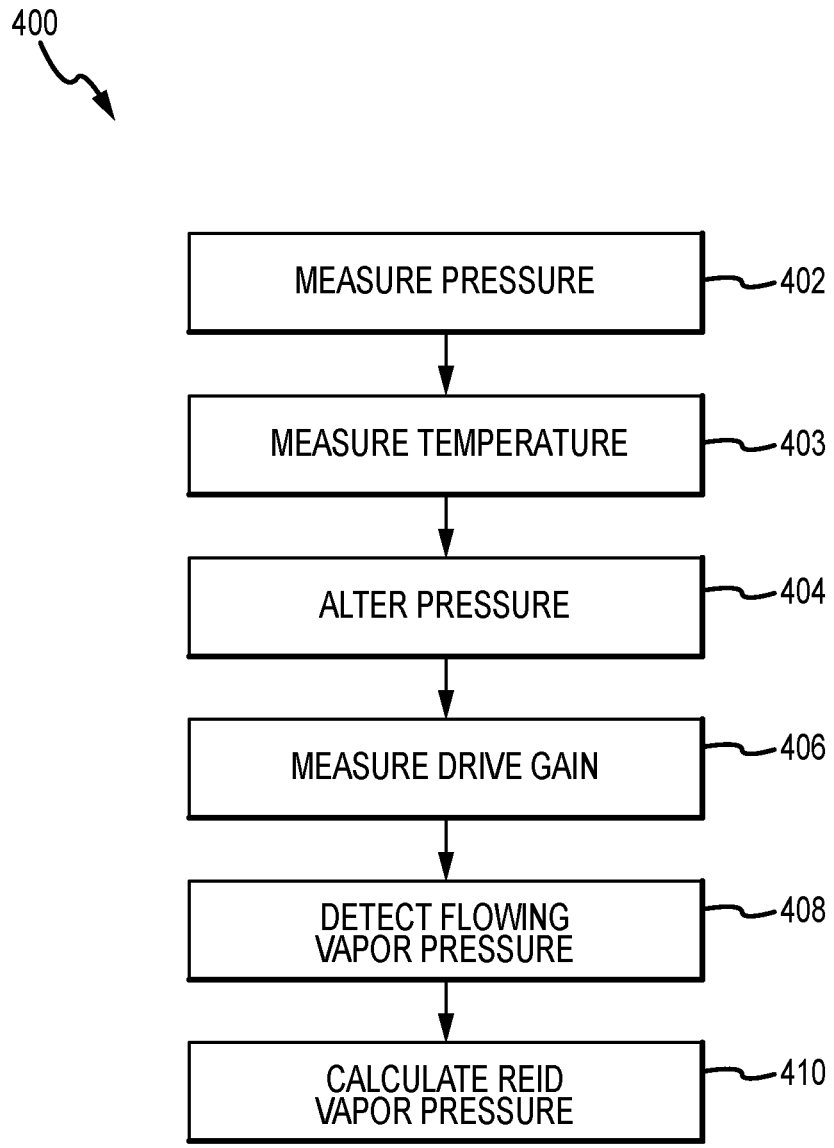
FIG. 5 illustrates another method of vapor pressure determination according to an embodiment.

Turning to FIG. 5, a flow chart 400 is provided that illustrates an example of a vapor pressure determination scheme employed by the system 300. The pressure of the process fluid in the system 300 is measured in step 402. This is accomplished with the pressure sensor 312. The temperature of the process fluid in the system 300 is measured in step 403. If the process fluid is single-phase under normal process conditions, the flowing pressure can be reduced by partially closing the upstream pressure regulator 308, as shown in step 404. Drive gain and/or density may be measured in step 406, and, as noted above, may be utilized to determine the presence of a multi-phase flow and also may be utilized to determine a monophasic/biphasic fluid phase boundary. As the pressure of the process fluid is being measured 402, and the pressure of the process fluid is being reduced 404, the introduction of a second phase is determined via drive gain and/or density measurements 406, which in turn indicates that the vapor pressure has been reached. The detection of the true vapor pressure is indicated in step 408 by recording both the pressure and temperature at the point where the presence of the second phase is detected. In step 410, the RVP is calculated from the measured true vapor pressure, taking into account the temperature at the time the true vapor pressure was recorded.

It should be noted that, if the process fluid already contains some vapor, this will be detected by measuring the drive gain and/or density, and the downstream pressure regulator 310 can be partially closed to increase pressure for the purpose of determining the vapor pressure and temperature at the point when the second phase is no longer present. In either case, it is the monophasic/biphasic fluid phase boundary and the related temperature/pressure of process fluid at this boundary that is utilized to indicate the true vapor pressure of the process fluid.

In other embodiments, other pressure regulators and methods of pressure control may be employed, should an upstream/downstream pressure regulator configuration not provide enough pressure change to reach the vapor pressure. In other embodiments, a temperature measurement could also be included, so to provide the ability to convert between true vapor pressure (TVP) and vapor pressure at standard temperature (e.g. Reid Vapor Pressure (RVP)). TVP is the actual vapor pressure of a liquid product at the measured temperature. TVP is difficult to directly measure and depends on the composition and temperature of the liquid in the measurement device. Once the TVP and temperature are known, the true vapor pressure at any other temperature and/or the RVP can be calculated from the empirical correlation data stored in meter electronics 20. The empirical correlation data may comprise look-up tables, mathematical algorithms, and/or mathematical curves. A direct RVP measurement typically requires sending samples for laboratory analysis.

In an embodiment, the system 300 is disposed in a slip stream that measures just a sample of the main flow stream, thus reducing impact on material processes. Because RVP is largely dependent on composition, a slip stream sample will be effective in cases where composition is reasonably homogenous. This allows the system to be smaller in size, less costly, and less obtrusive.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other vibrating systems, and not just to the embodiments described above and shown in the accompanying figures. Accordingly, the scope of the invention should be determined from the following claims.

We claim:

1. A method of determining vapor pressure of a fluid, comprising the steps of:
   providing a meter having meter electronics, wherein the meter comprises at least one of a flowmeter and a densitometer;
   flowing a process fluid through the meter;
   providing a low-pressure location in an outlet manifold of the meter;
   measuring a temperature of the process fluid at the low-pressure location;
   adjusting the static pressure of the process fluid until flashing is detectable at the low-pressure location; and
   determining the true vapor pressure of the process fluid at an instance where flashing is detectable.

2. The method of determining vapor pressure of a fluid of claim 1, wherein measuring the temperature comprises IR thermography.

3. The method of determining vapor pressure of a fluid of claim 1, wherein detecting the flashing comprises optical analysis.

4. The method of determining vapor pressure of a fluid of claim 1, wherein the low-pressure location comprises a differential pressure element.

5. The method of determining vapor pressure of a fluid of claim 1, comprising the steps of:
measuring the temperature of the process fluid; and
calculating the Reid Vapor Pressure from the temperature and the true vapor pressure.

6. The method of determining vapor pressure of a fluid of claim 5, comprising the step of measuring a vapor:liquid ratio at a time point where the true vapor pressure is measured; and
associating the vapor:liquid ratio with the Reid vapor pressure at the time point the true vapor pressure is measured.

7. A system (300) for determining true vapor pressure of a process fluid comprising:
a meter (5) comprising at least one of a flowmeter and a densitometer;
an outlet manifold comprising a low-pressure location;
a pressure regulator (308) in fluid communication with the meter (5);
a pressure sensor (312) in fluid communication with the process fluid;
a temperature sensor in the outlet manifold configured to measure a temperature at the low-pressure location;
meter electronics (20) in communication with the meter (5) and the pressure sensor (312), wherein the meter electronics (20) is configured to:
control the pressure regulator (308) to adjust a static pressure of the process fluid until flashing at the low-pressure location is detected by the temperature sensor; and
calculate a true vapor pressure of the process fluid at an instance where flashing is detectable.

8. The system (300) of claim 7, wherein the temperature sensor comprises an IR thermograph.

9. The system (300) of claim 7, wherein an optical sensor is configured to detect flashing.

10. The system (300) of claim 7, wherein the low-pressure location comprises a differential pressure element.

11. The system (300) of claim 7, wherein the meter electronics (20) is configured to:
measure a vapor:liquid ratio at a time point where the true vapor pressure is measured; and
associating the vapor:liquid ratio with a calculated Reid vapor pressure at the time point where the true vapor pressure is measured.

12. The system (300) of claim 7, wherein the meter (5) comprises:
one or more conduits (103, 103');
at least one driver (104) attached to the one or more conduits (103, 103') configured to generate a vibratory signal to the one or more conduits (103, 103'); and
at least one pickoff (105, 105') attached to the one or more conduits (103, 103') configured to receive a vibratory signal from the one or more conduits (103, 103').

* * * * *